United States Patent [19]

Omura et al.

[11] Patent Number: 4,626,547

[45] Date of Patent: Dec. 2, 1986

[54] ANTIBIOTIC AM-2604-A, AN ANTI-TRICHOMONAS AGENT, ANTI-CACCIDIUM AGENT, ANTI-VIRAL AGENT AND ANTI-FUNGAL AGENT CONTAINING THE SAME AND METHODS OF USE OF THE SAME

[75] Inventors: Satoshi Omura; Hideki Shimizu, both of Tokyo, Japan

[73] Assignee: The Kitasato Institute, Tokyo, Japan

[21] Appl. No.: 671,398

[22] Filed: Nov. 15, 1984

Related U.S. Application Data

[62] Division of Ser. No. 459,912, Jan. 21, 1983, Pat. No. 4,503,152.

[30] Foreign Application Priority Data

Jan. 21, 1982 [JP] Japan .................................. 57-6756

[51] Int. Cl.$^4$ .................. C07D 407/06; A61K 31/365
[52] U.S. Cl. ..................................... 514/450; 549/271
[58] Field of Search ......................... 549/271; 514/450

[56] References Cited

FOREIGN PATENT DOCUMENTS 0042697 3/1982 Japan .................................. 549/271

Primary Examiner—Jane T. Fan
Attorney, Agent, or Firm—Sughrue, Mion, Zinn, Macpeak, and Seas

[57] ABSTRACT

An antibiotic substance designated as AM-2604-A is described, and is obtained by cultivating an antibiotic AM-2604-A substance-producing strain belonging to the genus Streptomyces in a nutrient medium and recovering the desired substance from the culture broth.

18 Claims, 4 Drawing Figures

ANTIBIOTIC AM-2604-A, AN ANTI-TRICHOMONAS AGENT, ANTI-CACCIDIUM AGENT, ANTI-VIRAL AGENT AND ANTI-FUNGAL AGENT CONTAINING THE SAME AND METHODS OF USE OF THE SAME

This is a division of application Ser. No. 459,912 filed Jan. 21, 1983, now U.S. Pat. No. 4,503,152, now issued Mar. 5, 1985.

FIELD OF THE INVENTION

The present invention relates to a novel antibiotic AM-2604-A substance and a process for the production thereof.

SUMMARY OF THE INVENTION

In the course of extensive investigations on actinomycetes, it has been found that Streptomyces sp. AM-2604 which has been isolated from soil produces a novel antibiotic substance.

The present invention relates to:

(1) a novel antibiotic AM-2604-A substance having physical and chemical properties as described hereinafter; and (2) a process for producing said antibiotic AM-2604-A substance by cultivating a strain belonging to the genus Streptomyces and capable of producing the antibiotic AM-2604-A substance in a culture broth.

DETAILED DESCRIPTION OF THE INVENTION

The physical and chemical properties of the antibiotic AM-2604-A substance of the invention are as follows:

(1) Elemental Analysis (%): C: 64.29–64.97; H: 8.00–8.63; N: 1.45–1.69; O: 21.91–25.59.

It is considered that the antibiotic AM-2604-A substance rarely shows the definite elemental analytical values in view of its properties. Using a purified sample having a purity of 99.5% or more, an elemental analysis was performed twice, and the results are as follows:

Run No. 1: C: 64.31; H: 8.62; N: 1.54; O: 25.53.

Run No. 2: C: 64.71; H: 8.03; N: 1.68; O: 25.58.

(2) Optical Rotation:

$[\alpha]_D^{27.5} = +240°$ (C=0.02, methanol).

(3) Melting Point:

204°–205° C.

(4) Mass Spectrum

A mass spectral (FD mass spectral) analysis showed a big peak at a mass number of 638, and other peaks at 639, 656, and 657.

(5) Ultraviolet Absorption Spectrum

Figure 1:
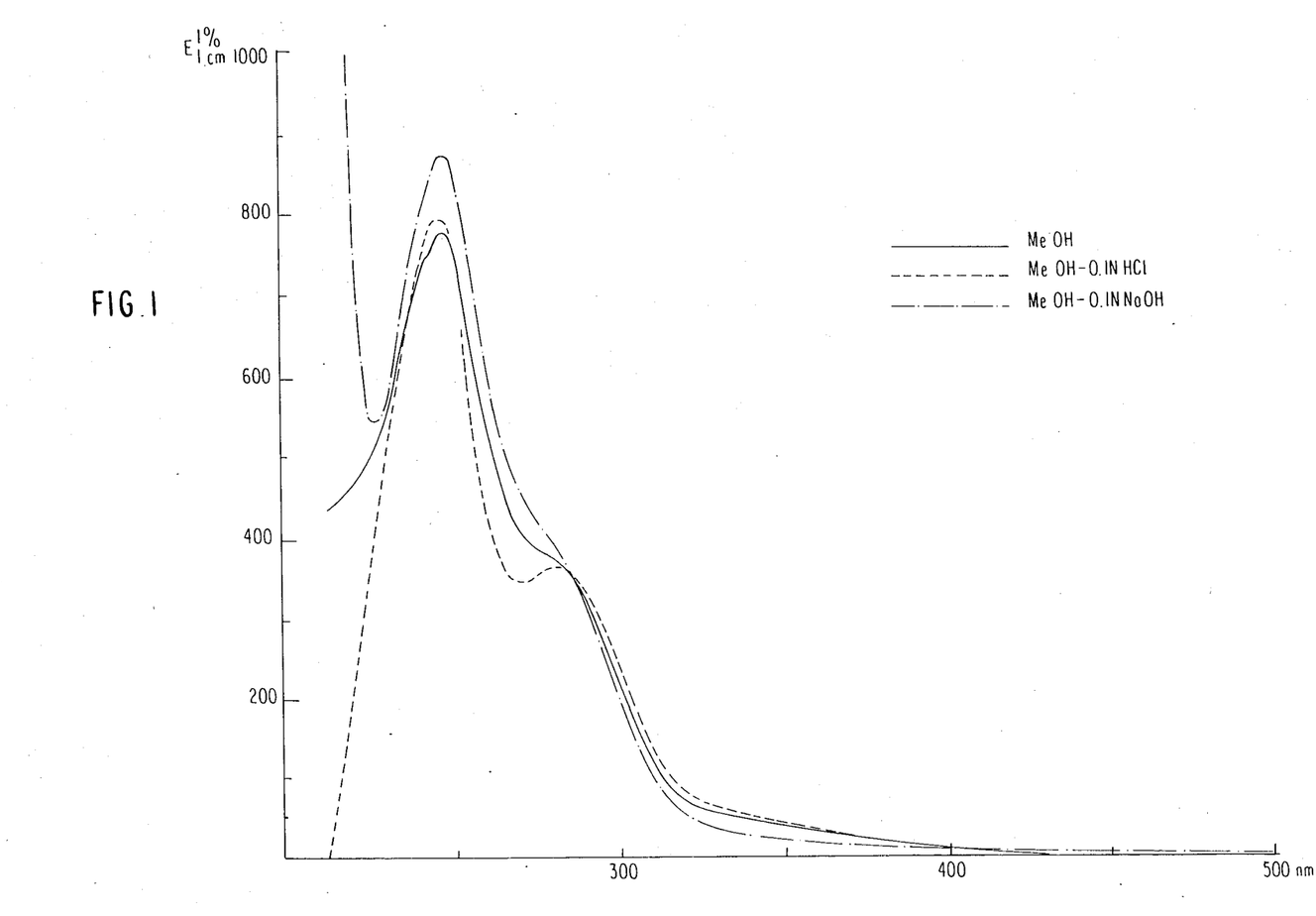
FIG. 1 is an ultraviolet absorption spectrum of the antibiotic AM-2604-A substance of the invention.

Shown in FIG. 1. The absorption maximums ($E_1$ $_{cm}1\%$) in methanol are: 248 nm (780), 280 nm shoulder (372), and 330 nm shoulder (54). The absorption maximums in 0.1N-HCl acidic methanol are: 247 nm (795), 281 nm (362), and 330 nm shoulder (66). The absorption maximums in 0.1N-NaOH basic methanol are: 248 nm (875), 280 nm shoulder (400), and 330 nm shoulder (37).

(6) Infrared Absorption Spectrum

Figure 2:
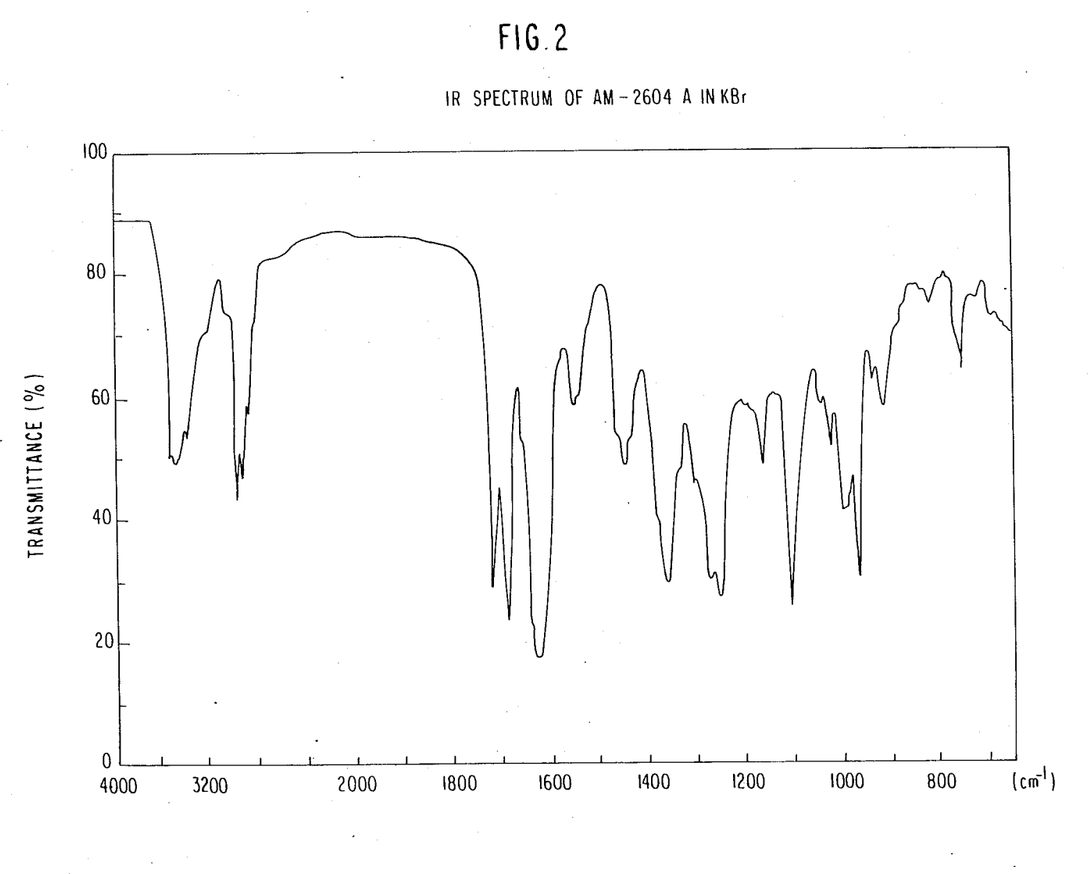
FIG. 2 is an infrared absorption spectrum of the antibiotic AM-2604-A substance of the invention.

Shown in FIG. 2.

(7) Proton Nuclear Magnetic Resonance Spectrum

Figure 3:
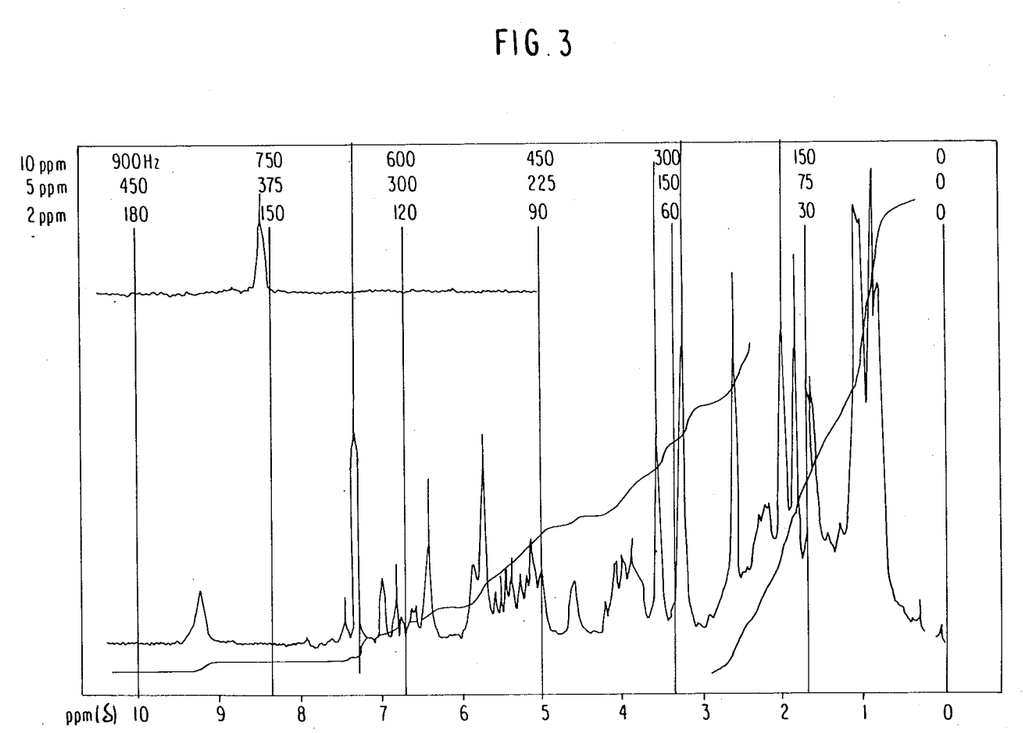
FIG. 3 is a proton nuclear magnetic resonance (NMR) spectrum of the antibiotic AM-2604-A substance of the invention.

Shown in FIG. 3.

(8) $^{13}$C Nuclear Magnetic Resonance Spectrum

Figure 4:
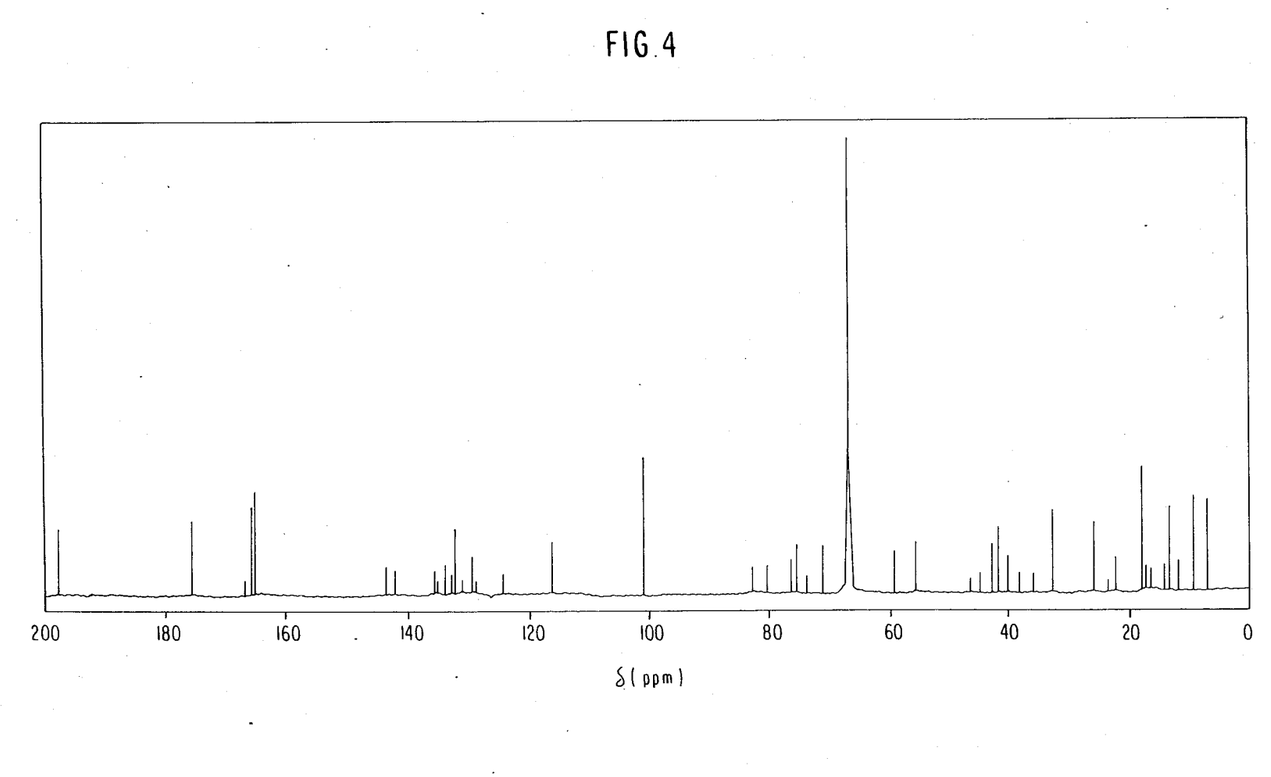
FIG. 4 is a $^{13}$C-NMR spectrum of the antibiotic AM-2604-A substance of the invention.

Shown in FIG. 4.

(9) Solubility in Solvents

Soluble in organic solvents such as chloroform, acetone, and ethyl acetate, sparingly soluble in lower alcohols, and insoluble in n-hexane and water.

(10) Color Reactions

Positive to a ferric chloride reaction, a permanganic acid reaction, an anisaldehyde sulfuric acid reaction, and a p-anisidine hydrochloric acid salt reaction. Negative to a Dragendorff reaction and a ninhydrin reaction.

(11) Color of the Substance

Pale yellow (12) Rf Values

Measured on silica gel thin layer chromatography (TLC aluminum sheet produced by Merck & Co.; silica gel, 60F$_{254}$; thickness, 0.2 mm) by the usual method.

|  | Rf |
| --- | --- |
| (a) Chloroform/methanol (9:1) | 0.54 |
| (b) Chloroform/methanol (4:1) | 0.73 |
| (c) Benzene/acetone (1:1) | 0.58 |
| (d) Benzene/methanol (2:1) | 0.70 |
| (e) Ethyl acetate | 0.36 |
| (f) Ethanol/water (4:1) | 0.81 |

In view of the above-described physical and chemical properties of the antibiotic AM-2604-A substance and those of derivatives therefrom, it is believed that the antibiotic AM-2604-A substance is a compound having the molecular formula of $C_{48}H_{71}NO_{14}$ and the following structural formula:

The biological properties of the antibiotic AM-2604-A substance are hereinafter described.

(1) Antimicrobiological Properties

The minimum inhibitory concentrations (MIC) of the antibiotic substance as determined by the agar dilution method are shown in Table 1 below.

TABLE 1

| Test Organism | MIC (mcg/ml) |
| --- | --- |
| Staphylococcus aureus ATCC 65389 | >100 |
| Bacillus subtilis ATCC 6633 | >100 |
| Micrococcus luteus ATCC 9341 | >100 |
| Mycobacterium smegmatis ATCC 607 | >100 |
| Escherichia coli NIHJ | >100 |
| Proteus vulgarius IFO 3167 | >100 |
| Xanthomonas oryzae | >50 |
| Candida albicans | >100 |
| Saccharomyces sake | 100 |
| Microsporum gypseum | 50 |
| Trichophyton interdigitale | 50 |
| Aspergillus niger | >100 |
| Piricularia oryzae | 12.5 |
| Alternaria kikuchiana | >50 |
| Mucor racemosus | 50 |
| Fusarium oxysporum | >100 |
| Monilinia fructicola | 12.5 |
| Botrytis cinerea | >50 |

(2) Growth Inhibitory Action against Various Viruses

The antiviral activity of the antibiotic substance was determined by the degree of reduction (inhibitory rate) in the rate of plaque-formation by virus. In this determination, primary chick embrionic cells (CE cells) were used, and the following eight types of virus were tested:

RNA type virus: Vesicular stomatitis virus (VSV), Sindbis virus (Sb), Western equine encephalitis virus (WEE), and Newcastle disease virus (NDV), and DNA type virus: Herpes virus Type No. 1 (HSV-1) and Type No. 2 (HSV-2), and DIE strain of vaccinia virus (Vac-DIE) and IHD strain of vaccinia virus (Vac-IHD).

The inhibitory activity of the antibiotic substance against each virus as described above was measured as follows:

Several 10-fold increasing dilutions of the antibiotic substance, the maximum concentration being 1 μg/ml, were prepared with an Eagle minimum essential medium containing 2% of calf serum (MEM/CS 2%). Each dilution was added to CE cells in a monolayer form, which had been cultivated on a Petri dish (diameter: 4 cm), and the cells were incubated in a $CO_2$ incubator at 37° C. for 20 hours. At the end of the time, the antibiotic substance was removed, and the cells were washed with phosphate-buffered saline solution (pH 7.2). Thereafter, the cells were inoculated with about 100 PFU (PFU: plaque-formation unit) of each virus as described above, which was then allowed to adsorb at 37° C. for 1 hour and fixed by adding 1% agar-containing MEM/CS 2%. These cells were again placed in the $CO_2$ incubator and cultivated at 37° C. for the following predetermined time:

2 days in the case of VSV, Sb, and WEE;

3 days in the case of HSV-1 and HSV-2; and 4 days in the case of Vac-DIE, Vac-IHD, and NDV.

After the cultivation was completed, agar containing 0.01% of Neutral Red was added to the cells in a superposed layer formulation to dye living cells, and the number of plaques formed by the infection of the virus was counted.

Cells which were cultivated in a medium not containing the antibiotic substance were used as controls.

The antiviral activity, i.e., plaque-formation reduction rate (PR%) is defined as follows:

$$PR\% = \left(1 - \frac{\text{[Number of Plaques for Cells treated with the Antibiotic Substance]}}{\text{[Number of Plaques for Cells not treated with the Antibiotic Substance]}}\right) \times 100$$

A concentration of the antibiotic substance at which PR% is 50% is defined as a 50% effective dose ($ED_{50}$), and its value for each virus is shown in Table 2 below.

TABLE 2

| Virus | 50% Effective Dose ($ED_{50}$) (μg/ml) |
| --- | --- |
| RNA Virus | |
| VSV | 0.0003 |
| Sb | 0.0005 |
| WEE | 0.0003 |
| NDV | 0.0003 |
| DNA Virus | |
| Vac-DIE | 0.0003 |
| Vac-IHD | 0.0003 |
| HSV-1 | 0.0003 |
| HSV-2 | 0.0003 |

It can be seen from Table 2 that the antibiotic substance of the invention has high inhibitory activity against various DNA or RNA viruses. Thus, the antibiotic substance of the invention is believed to be a very useful substance.

(3) Effectiveness on Coccidium-Infected Chicken

The potency of the antibiotic substance on coccidium-infected chickens was determined as follows:

Two-week-old white leghorn male chicks were divided into four groups of ten each. The feed used in this assay was a commercially available chick-breeding standard feed (major components: 19% crude protein, 2.5% crude fat, 5.0% crude fiber, 8.0% crude ash, 0.7% calcium, and 0.55% phosphorus).

One day after the start of feeding, $2 \times 10^4$ mature oocysts of *Eimeria tenella* per chick were orally administered to the chicks of the groups (Groups 1, 2 and 3) except for a non-infected control group (Group 4). Thereafter, the chicks of Groups 1 and 2 were bred by feeding the standard feed containing 0.005% and 0.01% of the antibiotic substance, respectively, and Groups 3 and 4 were bred by feeding only the standard feed.

During the breeding period, the weight of each chick was measured, and the blood in the feces was observed. Furthermore, the number of oocysts in the feces 7 days after the infection of the oocysts were counted, and the disorder of cecum was examined by necropsy. In this way, the anti-coccidium action of the antibiotic substance was determined. The results are shown in Table 3.

The items in Table 3 are as follows:

$$\text{Increment of Weight} = \frac{\text{[Average Weight at the End of Test]}}{\text{[Average Weight at the Start of Test]}} \quad (1)$$

Ratio of Increment of Weight = (2)

$$\frac{\text{[Increment of Weight for Test Group]}}{\text{[Increment of Weight for Non-infected Control Test Group]}}$$

(3) Blood Bleeding

The amount of blood from the intestine of the chick is judged from the number of blood stains.

(4) Disorder of Cecum
- Normal
± Minor
+ Minor, but slight disorder is observed.
+ + Moderate hypertrophy is observed.
+ + + Serious (disorder is very significant)

(5) Number of Oocysts

Number of oocysts per gram of the feces 7 days after the infection

As apparent from the results of Table 3, the AM-2604-A substance of the invention has an excellent anticoccidium action.

(4) Effectiveness on *Trichomonas foetus*-Infected Mice

An infection-therapy test of *Trichomonas foetus*-infected mice was performed as follows:

Mice were divided into groups of ten. *Trichomonas foetus* was cultivated at 37° C. on a Trichocel broth with 5% inactivated calf serum added (produced by BBL Co.) for 48 hours. One milliliter of the *Trichomonas foetus*-containing solution ($4 \times 10^6$ cells/ml) was injected intraperitoneally into mice having a weight of about 20 g. Immediately after the injection, the antibiotic substance was orally administered in an amount of 2 mg/kg or 1 mg/kg in the form of a CM (carboxymethyl) cellulose suspension, and thereafter, the administration was performed once a day for three consecutive days.

The infection-therapy effect was judged as follows:

Seven days after the injection of *Trichomonas foetus*, the formation of ascites was examined. In the case of mice in which ascites was formed, the ascites were taken out and the presence of *Trichomonas foetus* was examined using a microscope. In connection with those mice in which the formation of ascites did not occur, their intraperitones were washed with 1 ml of sterilized physiological saline solution, and the presence of *Trichomonas foetus* in the washing liquid was examined using a microscope. the therapy effect was judged from the presence of *Trichomonas foetus*, the formation of ascites and the ratio of living mice. The results are shown in Table 4.

As apparent from the results of Table 4, the antibiotic AM-2604-A substance of the invention has an excellent anti-trichomonas action.

TABLE 4

|  | Drug Amount Administered (mg/kg) | Number of Mice That Died | Living Mice with Formation of Ascites | Mice with *Trichomonas foetus* | Cured Mice |
| --- | --- | --- | --- | --- | --- |
| Drug-Administered Group | 8 | 1/10 | 1/10 | 2/10 | 8/10 |
|  | 4 | 2/10 | 2/10 | 5/10 | 5/10 |
| Drug-Non-Administered Control Group | 0 | 7/10 | 3/10 | 10/10 | 0/10 |

The toxicity testing of the antibiotic AM-2604-A substance was performed using mice by the intraperitoneal injection method. It was found that $LD_{50}$ was 3 mg/kg.

TABLE 3

| | Weight | | | Blood Bleeding | | | Disorder of Cecum | | | | | Number of Oosysts (on the average) |
| --- | --- | --- | --- | --- | --- | --- | --- | --- | --- | --- | --- | --- |
| | Average Weight at the Start of Test | Increment of Weight | Ratio of Increment of Test | 5th Day | 6th Day | 7th Day | − | ± | + | + + | + + + | |
| Drug-Administered Group | | | | | | | | | | | | |
| Group 1 0.005% AM-2604-A Administered | 104.5 | 1.83 | 0.99 | Not observed | Not observed | Not observed | 8/10 | 1/10 | 1/10 | — | — | $1.7 \times 10^4$ |
| Group 2 0.01% AM-2604-A Administered | 104.2 | 1.86 | 1.01 | Not observed | Not observed | Not observed | 9/10 | 1/10 | — | — | — | 0 |
| Control Group | | | | | | | | | | | | |
| Group 3 Infected | 104.0 | 1.67 | 0.90 | Abundantly observed | Abundantly observed | Slightly observed | — | — | — | 1/10 | 9/10 | $2.5 \times 10^6$ |
| Group 4 Infected | 104.3 | 1.85 | 1.00 | Not observed | Not observed | Not observed | 10/10 | — | — | — | — | 0 |

As described above, the antibiotic AM-2604-A substance of the invention has little antibacterial activity against Gram-positive and Gram-negative bacteria, but is active against fungi, virus, coccidium, and trichomonas. Therefore, the antibiotic AM-2604-A substance is useful as an antifungal agent, an antiviral agent, an anticoccidium agent and an anti-trichomonas agent. Accordingly, the antibiotic AM-2604-A substance of the invention can be used for the prevention or treatment of human, animal and plant diseases due to fungi, virus, coccidium, and trichomonas.

When the antibiotic AM-2604-A substance of the invention is used as an anti-trichomonas agent, it can be administered by various techniques such as intravenous injection, subcutaneous injection, intraperitoneal administration, and rectal infusion in the form of a suppository. It is to be noted that the oral administration as shown in the above-described experiment is given by way of illustration. The antibiotic AM-2604-A substance of the invention can be shaped in any suitable form depending on the process of administration. In the preparation of oral administration agents, carriers or diluents, such as $CaCO_3$, lactose, sucrose, gelatin, polyvinyl pyrrolidone, and cyclodextrin, are added to form tablets, pills, or capsules. In addition, depending on the use, enteric coating agent and the like can be prepared with the above-described compounds. Further, medicines applicable to mucous membrane and suppositories can be prepared using substrates such as cacao fat, laurin fat, polyethylene glycol, or a mixture thereof. As injectable solutions, a suspension, a solution, or a powder to be dissolved can be used.

When the antibiotic AM-2604-A substance of the invention is used as an anti-trichomonas agent, its administration dose and schedule can be determined appropriately taking into consideration the symptoms of patient. The administration dose is usually from 0.02 to 10 mg/kg-weight, and the number of administration is from 1 to 6 per day. It is preferred that the administration is performed for consecutive days or with suitable intervals, depending on the improvements of the symptoms.

By comparing the physical and chemical properties, and biological characteristics of the antibiotic AM-2604-A substance with those of the known antibiotic substances, it has been found that the antibiotic AM-2604-A substance is a novel antibiotic substance.

Similar known antibiotic substances which are lipophilic, have the absorption maximums in the vicinity of 240 nm, 248 nm, and 330 nm in the ultraviolet absorption spectrum, and are active against fungi are SF-1540-A (Meiji Seika Nempo, 17, 16–24 (1978)), SF-1540-B (Meiji Seika Kenkyu Nempo, 17, 16–24 (1978)), and Setamycin (J. Antibiotics, 34, (10), 1253–1256 (1981)). Their melting points and optical rotations are as follows:

|  | Melting Point (°C.) | Optical Roration (°C.) |
| --- | --- | --- |
| SF-1540-A | 131–133 | +31.6 |
| SF-1540-B | 85–90 | +39 |
| Setamycin | 134–135 | +18.3 |

On the other hand, the antibiotic AM-2604-A substance has a melting point of 204°–205° C. and an optical rotation of +240°, which are significantly different from the above-listed values of the known antibiotic substances.

Furthermore, the antibiotic AM-2604-A substance is different from the known antibiotic substances in that the former substance is almost inactive against Gram-positive bacteria, whereas the latter substances are active against Gram-positive bacteria.

The antibiotic AM-2604-A substance of the invention can be prepared by cultivating an antibiotic AM-2604-A substance-producing microorganism belonging to the genus Streptomyces in a nutrient medium under aerobic conditions to accumulate the antibiotic AM-2604-A substance in the nutrient medium and in the microorganism, and recovering the antibiotic AM-2604-A substance therefrom.

Examples of the microorganisms which can be used in the production of the antibiotic AM-2604-A substance of the invention is Streptomyces sp. AM-2604 which has been isolated from a soil sample collected in Tachikawa-City, Tokyo, Japan. This strain was deposited with the Fermentation Research Institute, Agency of Industrial Science and Technology, under the accession number FERM BP-234 on Dec. 19, 1981.

The characteristics of the Streptomyces sp. AM-2604 are as follows:

(1) Morphological Characteristics

Vegetative mycelium develops abundantly in both natural and synthetic media, and usually does not have septal walls. Aerial mycelium is abundantly developed on media such as yeast malt agar, oatmeal agar, starch inorganic salt agar, glucose asparagine agar and glycerol asparagine agar, but is poorly developed or is not developed on media such as glycerol calcium malate agar, glucose peptone agar and nutrient agar. The aerial mycelium is white or gray, and is velvety or cottony. Microscopic analysis shows that the sporophore are spiral or loop type and have more than ten spores are linked. The spore has a size of 1.3–1.5×0.8 μm and is nearly oval. The surface of the spore is warty. Sclerotic granucles, sporangia, and zoospores have not been observed.

(2) Culture and Physiological Characteristics

The culture characteristics were examined according to the method as described in E. B. Shirling and D. Gottlieb, *International Journal of Systematic Bacteriology*, Vol. 16, page 313 (1966). The known culture media and experimental methods were also used in combination. The results are shown in Table 5. Color tone was determined according to *Color Harmony Manual*, 4th Ed. (Container Corporation of America, Chicago (1958)), and its code is listed in parentheses in Table 5. The observation was performed for each culture medium after culturing 2 weeks at 27° C. The physiological characteristics are shown in Table 6.

TABLE 5

|  | Growth | Reverse | *Aerial mycelium* | Soluble pigment |
| --- | --- | --- | --- | --- |
| Yeast extract-malt extract agar (ISP)* | good, raised, bamboo (2 gc) | gold (21 c) | moderate, cottony, white ashes (a 5 fe) | none |
| Oatmeal agar (ISP)* | good, penetrated light ivory (2 ca) | light ivory (2 ca) | good, velvety, pussywillow gray (5 dc) | none |
| Inorganic salts-starch agar (ISP)* | good, light ivory (2 ca) | light ivory (2 ca) | good, velvety, ashes (5 fe) | none |
| Glycerol-asparagine agar (ISP)* | good, raised, pearl (2 ba) | light ivory (2 ca) | moderate, velvety, oyster white (b) | none |
| Glucose-asparagine agar | good, raised, light ivory (2 ca) | light ivory (2 ca) | moderate, velvety, oyster white (b) | none |
| Peptone-yeast extract iron agar (ISP)* | poor, light wheat (2 ea) | light wheat (2 ea) | none | none |

TABLE 5-continued

| | Growth | Reverse | Aerial mycelium | Soluble pigment |
|---|---|---|---|---|
| Tyrosine agar (ISP)* | thin, yellow tint (1 ba) | yellow tint (1 ba) | none | none |
| Sucrose-nitrate agar** | good, light wheat (2 ea) | light wheat (2 ea) | moderate, velvety, white (a) | none |
| Glucose-nitrate agar** | moderate, light wheat (2 ea) | light wheat (2 ea) | none | none |
| Glycerol-calcium-malate-agar** | good, penetrated, parchment (1 cb) | parchment (1 cb) | poor, white (a) | none |
| Glucose-peptone agar** | good, light wheat (2 ea) | light wheat (2 ea) | none | none |
| Nutrient agar* | poor, light ivory (2 ca) | light ivory (2 ca) | none | none |

*Medium recommended by the International Streptomyces Project.
**Medium recommended by S. A. Waksman, see The Actinomyces, Vol. II, published by the Williams & Wilkins Co., Baltimore (1961).

TABLE 6

| | |
|---|---|
| Melanin formation | − |
| Tyrosinase reaction | − |
| $H_2S$ production | − |
| Nitrate reduction | + |
| Liquefaction of gelatin (20° C.) | + |
| Hydrolysis of starch | + |
| Coagulation of milk (37° C.) | + |
| Peptonization of milk (37° C.) | + |
| Cellulolytic activity | − |
| Temperature range for growth | 15–40° C. |
| Utilization of carbon sources (+ = utilizable) | |
| D-glucose | + |
| L-arabinose | + |
| D-xylose | + |
| D-mannitol | + |
| D-fructose | + |
| L-rhamnose | + |
| i-inositol | + |
| sucrose | + |

(3) Composition of Cell Wall

Diaminopimelic acid is of LL type, and arabinose and galactose are not observed.

The morphological characteristics of the present strain are summarized as follows:

The cell wall composition contains LL-diaminopimelic acid. Morphologically, sporophore are spiral and loop type and the surface of the spore is warty. The vegetative mycelium is light yellow, and the aerial mycelium is white or gray. It does not produce any soluble pigments and melamine.

It is thus believed that the present strain belongs to the genus Streptomyces, and is a strain belonging to the white or gray series according to the classification of T. G. Pridham and H. D. Tresner (*Bergey's Manual of Determinative Bacteriology*, 8th Ed., pp. 748–829 (1974)).

Any antibiotic AM-2604-A substance-producing strains belonging to the genus Streptomyes can be used in the invention, as well as the above-described Streptomyces sp. AM-2604 and its variants.

Those variants produced by changing the Streptomyces sp. AM-2604 by artificial variation techniques using ultraviolet rays, X rays, radiation rays, chemicals, etc. are, of course, microorganisms belonging to the genus Streptomyces, and all variants having the ability of producing the antibiotic AM-2604-A substance can be used in the invention.

Culture media containing nutrient sources such as carbon sources, nitrogen sources, and inorganic salts, as commonly used in the cultivation of known microorganisms, can be used in the cultivation of the antibiotic AM-2604-A substance-producing strain. Carbon sources may be assimiable carbon compounds, for example, glucose, maltose, lactose, sucrose, starch, dextrin, glycerin, and molasses. Nitrogen sources may be assimiable nitrogen compounds, for example, soybean powder, corn steep liquor, cotton seed powder, peptone, meat extract, yeast extract, dry yeast, casein hydrolytic products, ammonium salts, and nitric acid salts. In addition, if necessary, salts such as phosphoric acid salts, magnesium, potassium, calcium, sodium, iron and manganese can be used in the preparation of media.

In accordance with the process of the invention, the antibiotic AM-2604-A substance-producing strain is cultivated usually under aerated conditions. Agitated cultivation under aerated conditions is usually suitable. The cultivation temperature can be regulated within the range that the microorganism can grow, producing the antibiotic AM-2604-A substance. The particularly preferred temperature range is between 25° and 30° C. The pH is preferably from 6 to 7. The cultivation time is usually from about 50 to 100 hours although it varies with other various cultivation conditions such as compositions of culture media, cultivation temperature, pH, aerated condition and the like. The cultivation is completed in a suitable time as determined taking into consideration the time at which the maximum titer of the antibiotic AM-2604-A substance is reached.

The antibiotic AM-2604-A substance thus produced is recovered from the culture broth by known techniques. An example of isolation and purification of the antibiotic AM-2604-A substance from the culture broth is shown below:

The culture broth is separated into a solid matter (cells) and a filtrate. The solid matter is extracted with, for example, acetone or ethyl acetate, or alternatively, after a methanol treatment, extracted with an organic solvent such as ethyl acetate or chloroform. The filtrate is extracted with organic solvents capable of dissolving the antibiotic AM-2604-A substance such as ethyl acetate and benzene. Thereafter, the antibiotic AM-2604-A substance is recovered by known techniques commonly used in the purification of fat-soluble substances. For example, the extract (an acetone layer or ethyl acetate layer) is concentrated under reduced pressure. The thus-formed precipitate is separated and washed with n-hexane, and thereafter, the antibiotic AM-2604-A substance is separated by silica gel column chromatography using mixed solvents of benzene and acetone as an elution solvent.

The assay and quantitative determination of the antibiotic AM-2604-A substance are performed by silica gel thin layer chromatography (silica gel 60F$_{254}$ (produced by Merck & Co.); thickness, 0.2 mm; elution solvent, benzene/acetone=1/1; Rf value of the antibiotic AM-2604-A substance, 0.58), and a biological assay method using RK-13 cells (rabbit kidney cells) and VSV (vescular stomatitis virus).

The following examples are given to illustrate the invention in greater detail. It will be noted that these examples are illustrative, and the invention is not limited thereto.

EXAMPLE 1

A seed medium was inoculated with a platinum-loopful of the Streptomyces sp. AM-2604-A, FERM BP-234, from slant culture, and cultivation was performed at 27° C. for 2 days. Thereafter, 70 liters of culture medium placed in a 100-liter jar fermentator was inoculated with the above-prepared seed culture in a proportion of 1%, and agitated cultivation was performed at 27° C. for 67 hours under aerated conditions. The seed medium contained 1.0% glucose, 2.0% starch, 0.5% yeast extract, 0.5% peptone, and 0.4% calcium carbonate, and the main culture medium contained 2.0% dextrin, 0.2% glucose, 1.5% soybean powder, 0.3% yeast extract, and 0.3% calcium carbonate. Each medium was sterilized at 121° C. for 15 minutes after the adjustment to pH 7.0.

The culture broth (70 liters) was centrifuged by means of a Scharples type centrifuge to obtain a solid material (cells). The solid material was extracted with 10 liters of a 60% acetone solution with stirring. The resulting solution was filtered to obtain a 60% acetone extract. The 60% acetone extract was concentrated to 5.2 liters under reduced pressure, and after the addition of 10 liters of ethyl acetate, re-extraction was performed while thoroughly stirring. The thus-obtained ethyl acetate extract was concentrated to 100 ml under reduced pressure and allowed to stand overnight at room temperature. Thereafter, the formed precipitate was filtered and dried to obtain 1.2 g of a crude substance.

The crude substance (1.1 g) was placed on a silica gel column (Kisel gel 60 (produced by Merck & Co.), 25 g) charged with benzene, and developed with 180 ml of benzene and eluted successively with 180 ml portions of benzene/acetone (5:1), (4:1), and (3:1). Active fractions (Fraction No. 31–55, 12 ml/fraction tube) obtained by the benzene/acetone (4:1) portion was concentrated to 10 ml under reduced pressure, and after the addition of 10 ml of acetone, was allowed to stand overnight at room temperature to obtain 680 mg of pale yellow needle-like crystals of the antibiotic AM-2604-A substance. The physical and chemical properties of the substance agreed with the ones described above.

EXAMPLE 2

A seed medium was inoculated with a platinum-loopful of the Streptomyces sp. AM-2604, FERM BP-234, from slant culture, and cultivation was performed at 27° C. for 2 days. Two 30-liter jar fermentators, each containing 20 liters of a medium, were inoculated with the above-prepared seed culture in a proportion of 1%, and agitated cultivation was performed at 27° C. for 67 hours under aerated conditions. The seed culture medium contained 1.0% glucose, 2.0% starch, 0.5% yeast extract, 0.5% peptone, and 0.4% calcium carbonate, and the main culture medium contained 2.0% dextrin, 0.2% glucose, 1.5% soybean powder, 0.3% yeast extract, and 0.3% calcium carbonate. Each medium was adjusted to pH 7.0 and, thereafter, sterilized at 121° C. for 15 minutes.

The culture broth (40 liters) was centrifuged by means of a Scharples type centrifuge to obtain a supernatant liquid. To this supernatant liquid, 17 liters of benzene was added and well stirred, and the benzene layer was obtained by centrifugation. This benzene extract was concentrated under reduced pressure to obtain 3.8 g of an oily crude substance.

The oily crude substance (3.5 g) was placed on a silica gel column (Kisel gel 60 (produced by Merck & Co.), 105 g) charged with benzene, developed with 420 ml of benzene, and eluted successively with 420 ml portions of benzene/ethyl acetate (1:1) and ethyl acetate. The thus-obtained active fractions (Fraction Nos. 43–64, 20 ml/fraction tube) were collected and concentrated to dryness under reduced pressure to obtain 28 mg of a yellow-orange tar-like substance. This substance was crystallized from acetone to obtain 12 mg of pale yellow needle-like crystals of the antibiotic AM-2604-A substance. The physical and chemical properties of the substance agreed with the ones described above.

While the invention has been described in detail and with reference to specific embodiment thereof, it will be apparent to one skilled in the art that various changes and modifications can be made therein without departing from the spirit and scope thereof.

What is claimed is:

1. An antibiotic AM-2604-A substance having the following properties:
   (a) Molecular formula: $C_{48}H_{71}NO_{14}$;
   (b) Optical rotation: $[\alpha]_D^{27.5} = +240°$ (C=0.02, methanol);
   (c) Melting point: 204° to 205° C.;
   (d) Ultraviolet absorption spectrum: as shown in FIG. 1;
   (e) Infrared absorption spectrum as shown in FIG. 2;
   (f) Proton nuclear magnetic resonance spectrum as shown in FIG. 3;
   (g) $^{13}C$ Nuclear magnetic resonance spectrum as shown in FIG. 4; and
   (h) Soluble in chloroform, acetone, and ethyl acetate, sparingly soluble in lower alcohols, and insoluble in n-hexane and water 2. An antibiotic AM-2604-A substance as in claim 1 having the additional properties:
   (i) a positive color reaction to: a ferric chloride reaction, a permanganic acid reaction, an anisaldehyde sulfuric acid reaction, and a p-anisidine hydrochloric salt reaction; a negative color reaction to a Dragendorff reaction and a ninhydrin reaction;
   (j) a pale yellow color;

(k) the following Rf values measured on silica gel thin layer chromatography, with the corresponding solvent:
(i) chloroform/methanol (9:1): -Rf: 0.54
(ii) chloroform/methanol (4:1): -Rf: 0.73
(iii) benzene/acetone (1:1): -Rf: 0.58
(iv) benzene/methanol (2:1): -Rf: 0.70
(v) ethyl acetate: -Rf: 0.36
(vi) ethanol/water (4:1): -Rf: 0.81.

3. An anti-trichomonas composition comprising a pharmaceutical effective amount of the antibiotic as defined in claim 1 as an active component and a pharmaceutically acceptable diluent or carrier.

4. An anti-coccidium composition comprising a pharmaceutical effective amount of the antibiotic as defined in claim 1 as an active component and a pharmaceutically acceptable diluent or carrier.

5. An anti-viral composition comprising a pharmaceutical effective amount of the antibiotic as defined in claim 1 as an active component and a pharmaceutically acceptable diluent or carrier.

6. An anti-fungal composition comprising a pharmaceutical effective amount of the antibiotic as defined in claim 1 as an active component and a pharmaceutically acceptable diluent or carrier.

7. An anti-viral composition as in claim 5, wherein said agent is an anti-DNA virus agent.

8. An anti-viral composition as in claim 5, wherein said agent is an anti-RNA virus agent.

9. The anti-trichomonas composition as in claim 3, wherein acceptable diluents or carriers are selected from the group consisting of $CaCO_3$, lactose, sucrose, gelatin, polyvinyl pyrrolidone and cyclodextorin.

10. A method for treating human, animal and plant diseases due to fungi comprising administering a pharmaceutically effective amount of the antibiotic as defined in claim 1.

11. A method for treating human, animal and plant diseases due to virus comprising administering a pharmaceutically effective amount of the antibiotic as defined in claim 1.

12. A method for treating human and animal diseases due to coccidium comprising administering a pharmaceutically effective amount of the antibiotic as defined in claim 1.

13. A method for treating human and animal diseases due to trichomonas comprising administering a pharmaceutically effective amount of the antibiotic as defined in claim 1.

14. The method as in claim 11, wherein said agent is administered orally, intravenously, subcutaneously, intraperitoneally or rectally in the form of a suppository.

15. The method as in claim 12, wherein said agent is administered orally, intravenously, subcutaneously, intraperitoneally or rectally in the form of a suppository.

16. The method as in claim 13, wherein said agent is administered orally, intravenously, subcutaneously, intraperitoneally or rectally in the form of a suppository.

17. A method as in claim 13, wherein when said antibiotic is used in the treatment of humans and animal diseases due to trichomonas, the administered dose is from 0.20-10 mg/kg of the subject and the number of administrations is from 1-6 per day.

18. The method as in claim 10, wherein said agent is administered orally, intravenously, subcutaneously, intraperitoneally or rectally in the form of a suppository.

* * * * *